(12) United States Patent
Thuemen

(10) Patent No.: US 12,171,403 B2
(45) Date of Patent: Dec. 24, 2024

(54) VIDEO ENDOSCOPE

(71) Applicant: OLYMPUS WINTER & IBE GMBH, Hamburg (DE)

(72) Inventor: Alrun Thuemen, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 715 days.

(21) Appl. No.: 17/419,421

(22) PCT Filed: Dec. 4, 2019

(86) PCT No.: PCT/EP2019/083760
§ 371 (c)(1),
(2) Date: Jun. 29, 2021

(87) PCT Pub. No.: WO2020/141037
PCT Pub. Date: Jul. 9, 2020

(65) Prior Publication Data
US 2022/0071481 A1    Mar. 10, 2022

(30) Foreign Application Priority Data

Jan. 4, 2019   (DE) .......................... 102019100147.1

(51) Int. Cl.
*A61B 1/00*    (2006.01)
*A61B 1/05*    (2006.01)

(52) U.S. Cl.
CPC ...... *A61B 1/00183* (2013.01); *A61B 1/00073* (2013.01); *A61B 1/00179* (2013.01); *A61B 1/05* (2013.01); *A61B 1/00066* (2013.01)

(58) Field of Classification Search
CPC ............ A61B 1/00183; A61B 1/00179; A61B 1/00066; A61B 1/00121; A61B 1/00128;
(Continued)

(56) References Cited

U.S. PATENT DOCUMENTS 4,697,577 A * 10/1987 Forkner ............. A61B 1/00183
600/173
5,716,354 A *  2/1998 Hluchy ............. A61B 18/1442
606/46

(Continued)

FOREIGN PATENT DOCUMENTS

DE   102010044786 A1 *  3/2012  ......... A61B 1/00071
DE   102011089132 A1 *  6/2013  ......... A61B 1/00096

(Continued)

OTHER PUBLICATIONS

International Search Report dated Mar. 10, 2020 issued in PCT/EP2019/083760.

(Continued)

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

A video endoscope including an elongated shaft, wherein the shaft includes at least one shaft tube, a magnetic ring surrounding the shaft tube is freely rotatably arranged in a region of a proximal end of the shaft tube, and the magnetic ring is axially fixed between a proximal stop shoulder of the shaft tube and a distal retaining body, and wherein the retaining body having a sleeve-like configuration and is placed onto the shaft tube from the distal direction. The shaft tube has an indentation in a region of the retaining body, and the retaining body is fastened on the shaft tube by a fastener which penetrates the retaining body and extends into the indentation.

11 Claims, 2 Drawing Sheets

(58) Field of Classification Search
CPC .......... A61B 1/00133; A61B 1/00135; A61B 1/00105
See application file for complete search history.

(56) References Cited

U.S. PATENT DOCUMENTS

| | | | | |
|---|---|---|---|---|
| 2007/0276180 | A1* | 11/2007 | Greenburg | A61B 90/57 600/106 |
| 2008/0204863 | A1 | 8/2008 | Vogeli | |
| 2011/0306834 | A1* | 12/2011 | Schrader | G02B 23/2484 600/109 |
| 2012/0136213 | A1 | 5/2012 | Weimer et al. | |
| 2014/0128674 | A1* | 5/2014 | Wieters | A61B 1/00181 600/160 |
| 2014/0128679 | A1* | 5/2014 | Wieters | A61B 1/00096 600/170 |
| 2014/0326223 | A1* | 11/2014 | Proettel | F02M 35/10209 123/559.1 |
| 2014/0357952 | A1* | 12/2014 | Krohn | A61B 1/00006 600/112 |
| 2015/0085093 | A1 | 3/2015 | Heni et al. | |
| 2016/0124211 | A1* | 5/2016 | Wieters | A61B 1/00071 359/367 |
| 2016/0206181 | A1* | 7/2016 | Kiedrowski | A61B 1/00128 |
| 2019/0117048 | A1* | 4/2019 | Wickersheim | A61B 1/00183 |

FOREIGN PATENT DOCUMENTS

| | | |
|---|---|---|
| DE | 102012202552 B3 | 7/2013 |
| DE | 102013108631 A1 | 2/2015 |
| EP | 0251478 A1 | 1/1988 |
| EP | 2850997 A1 | 3/2015 |
| WO | 2006056094 A1 | 6/2006 |

OTHER PUBLICATIONS

German Office Action dated Oct. 24, 2019 issued in 102019100147.1.

* cited by examiner

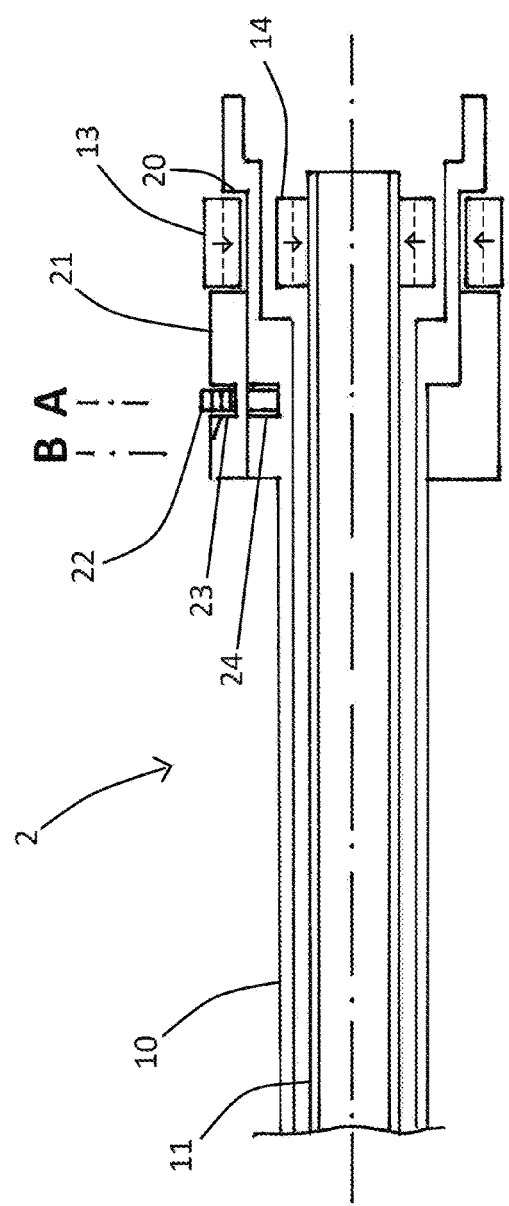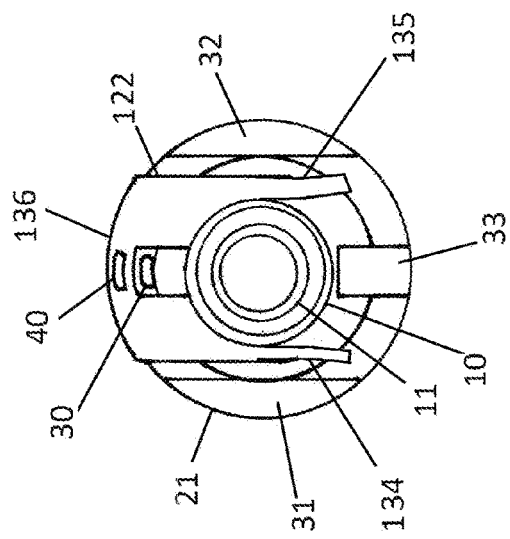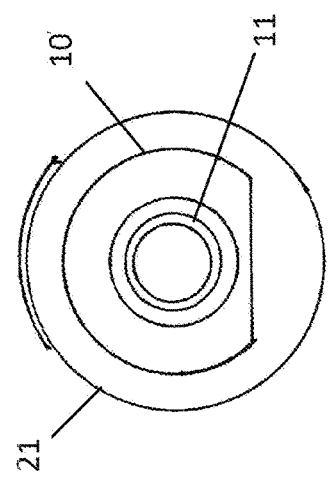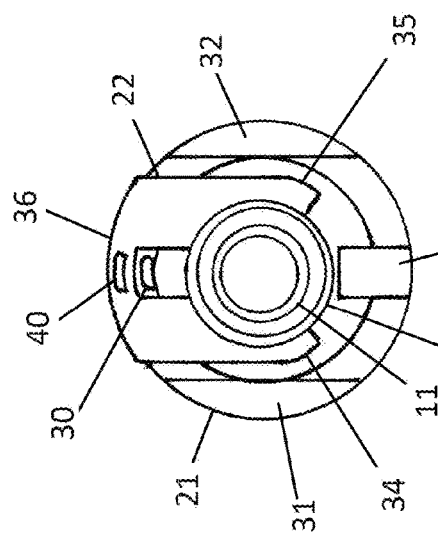

VIDEO ENDOSCOPE

CROSS-REFERENCE TO RELATED APPLICATION

The present application is based upon and claims the benefit of priority from PCT/EP2019/083760 filed on Dec. 4, 2019, which claims priority to DE 10 2019 100 147.1 filed on Jan. 4, 2019, the entire contents of each of which is incorporated herein by reference.

BACKGROUND

Field

The present disclosure relates to a video endoscope and more particularly to a video endoscope with an elongated shaft, wherein the shaft comprises at least one shaft tube, a magnetic ring surrounding the shaft tube is freely rotatably arranged in the region of a proximal end of the shaft tube, and the magnetic ring is axially fixed between a proximal stop shoulder of the shaft tube and a distal retaining body, and wherein the retaining body has a sleeve-like configuration and is placed on the shaft tube from the distal direction.

Prior Art

Video endoscopes are used in medicine to examine and, if necessary, treat areas of a patient that are difficult to access. For this purpose, they have an elongated shaft, the distal end of which is guided to the site to be examined.

A video camera is located at the distal end of the shaft and its signal is directed to the proximal end of the shaft and out of the endoscope. The signal is then routed to a monitor for display. The video camera of a video endoscope comprises a lens and an image sensor, which may be a CCD or CMOS chip, for example.

The lens of a video endoscope is often configured to have a viewing direction deviating from the longitudinal axis of the shaft. In this context, the viewing direction is referred to as the object-side optical axis of the lens. For this purpose, the objective may comprise a prism assembly. Corresponding video endoscopes are also referred to as 'side viewing' video endoscopes.

Side viewing video endoscopes allow a particularly large field of view to be covered by rotating the video endoscope about the longitudinal axis of the shaft. However, the problem arises that when the video endoscope is rotated, the image sensor also rotates. This causes the horizontal position of the image displayed on a monitor, for example, to be lost, which can cause a physician using the system to lose orientation on the image.

To prevent this, the image sensor is mounted in the video endoscope in such a way that it can be rotated around the longitudinal axis of the shaft. If the video endoscope is now rotated, the image sensor can be rotated in the opposite direction so that it retains its original orientation. This also preserves the horizontal position of the image.

A torque required to rotate the image sensor is usually applied at the proximal end of the video endoscope, for example via a rotating ring, and transmitted through the wall of a shaft tube of the video endoscope into its interior by means of a magnetic coupling without contact. For this purpose, a magnetic ring, which is connected to the rotating ring, is rotatably arranged on the outside of the shaft tube.

The shaft tube has a stop shoulder at its proximal end, against which the magnetic ring rests directly or indirectly. To prevent the magnetic ring from moving in the distal direction, a sleeve-like retaining body is arranged distally from the magnetic ring. The retaining body is placed on the shaft tube from the distal direction and pushed up to the magnetic ring. The retaining body is then fixed there on the shaft tube.

The retaining body is usually fixed to the shaft tube by means of several screws that are screwed into the retaining body around the circumference of the shaft tube and clamp it to the shaft tube. For this purpose, threaded holes must be made in the retaining body, which is costly. In addition, the screws must be coated with thread locking fluid after being screwed in to prevent them from loosening. All in all, therefore, many steps are necessary in order to manufacture such an endoscope.

SUMMARY

It is therefore an object to provide a video endoscope which is improved with respect to the problems described.

Such object can be achieved by a video endoscope with an elongated shaft, wherein the shaft comprises at least one shaft tube, a magnetic ring surrounding the shaft tube is freely rotatably arranged in the region of a proximal end of the shaft tube, and the magnetic ring is axially fixed between a proximal stop shoulder of the shaft tube and a distal retaining body, and wherein the retaining body has a sleeve-like configuration and is placed on the shaft tube from the distal direction, which is further configured in that the shaft tube has an indentation in the region of the retaining body, and the retaining body is fastened on the shaft tube by a fastening element which penetrates the retaining body and extends into the indentation.

The extension of the fastening element into the indentation creates a positive fit between the shaft tube, the retaining body and the fastening element, which provides a simple and secure fixation of the retaining body to the shaft tube.

The fastening element may be guided or guidable with a substantially linear movement through the retaining body and into the indentation. This allows the fastening element to be inserted particularly quickly and easily without the need for, for example, a screwing movement.

The indentation may be a circumferentially extending groove which extends along a circumferential angle of at least 180°, such as at least 270°, of the shaft tube.

The fastening element may comprise a U- or C-shaped bracket. A U-shaped or C-shaped bracket is understood to be a bracket having two arm-like free end portions connected to each other such as by a curved connecting portion. While in the case of a U-shaped clamp the distance between the end sections initially increases starting from the connecting section and then remains constant until the end of the end sections, the end sections of a C-shaped clamp approach each other again before the end thereof. Here, the above explanations explicitly refer to the initial shape of the clamp without taking elastic deformation into account.

The fastening element may engage the groove over a circumferential angle of more than 180°. This means that the circumferential angle between the outermost engagement point of one end portion of the fastening element, along the connecting portion, to the outermost engagement point of the other end portion of the fastening element can be more than 180° without the fastening element necessarily engaging the groove at every point of the specified circumferential angle.

The fastening element may be elastically deformed at least temporarily during insertion into the groove. Thereby, the fastening element, in its fully inserted position, may be at least partially sprung back to its initial shape, so that the fastening element is positively held in the groove. Being positively held in this context refers to a fastening element that may only be removed from the groove again by means of a deformation.

Similarly, the fastening element, in its fully inserted position, may be at least partially elastically deformed so that the fastening element may be frictionally held in the groove. Being frictionally held means that there may be a frictional force between the fastening element and the base of the groove which counteracts removal of the fastening element from the groove.

The fastening element may have a recess into which a tool for removing the fastening element may engage.

The shaft tube and the retaining body may comprise form-complementary guide elements which prevent the retaining body from rotating on the shaft tube.

BRIEF DESCRIPTION OF THE DRAWINGS

The embodiments are explained in more detail below with reference to some exemplary drawings. In doing so, the illustrated embodiments are merely intended to facilitate understanding of the invention without limiting it, in which:

FIG. 2 illustrates the internal structure of the shaft of a video endoscope in a longitudinal section, FIG. 3 illustrates the internal structure of the shaft of FIG. 2 in a cross-section, FIG. 4 illustrates a further cross-section through the shaft of FIG. 2, and FIG. 5 illustrates a cross-section through the shaft of another video endoscope.

DETAILED DESCRIPTION

Figure 1:
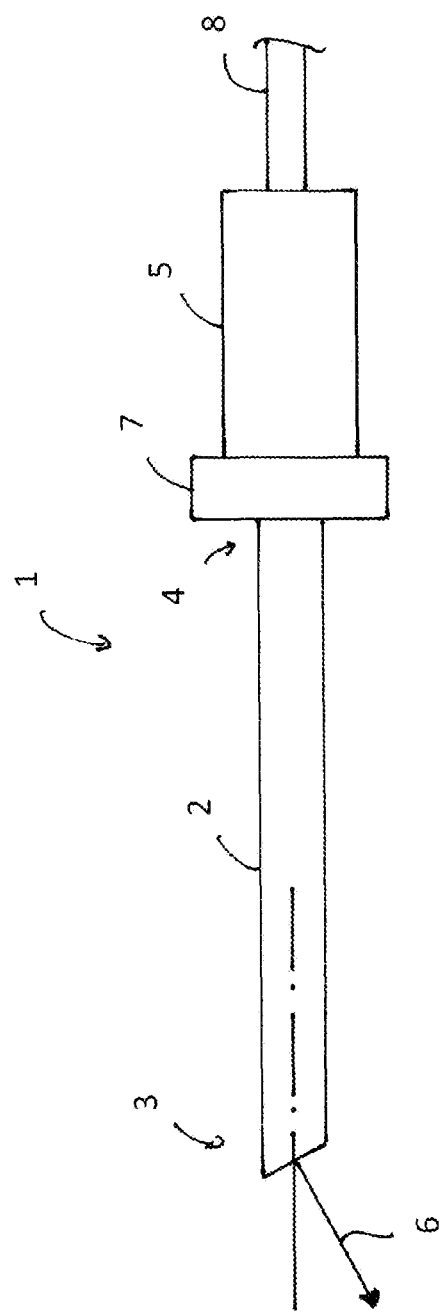
FIG. 1 illustrates a video endoscope.

FIG. 1 shows a video endoscope 1. The video endoscope 1 has an elongated shaft 2 with a distal end 3 and a proximal end 4. At the proximal end 4 of the shaft 2, a handle 5 is disposed, by means of which the video endoscope 1 may be held and operated.

At the distal end 3 of the shaft 2, a lens not shown is disposed, the viewing direction of which is aligned in the direction of the arrow 6. By rotating the video endoscope 1, the viewing direction of the lens may be rotated about its longitudinal axis. A rotating ring 7 is used to control the horizontal position of an image captured by the video endoscope 1. The video signals generated by the video endoscope 1 are output via a cable 8.

In FIG. 2, the internal structure of the shaft 2 is shown in simplified form. The shaft 2 comprises an outer shaft tube 10 and an inner shaft tube 11 disposed within the outer shaft tube 10. The lens is disposed at the distal end of the outer shaft tube 10, which is not shown. The outer shaft tube 10 is fixedly connected to the handle 5 of the video endoscope (not shown in FIG. 2), so that turning the handle 5 rotates the outer shaft tube 10 and thus also the lens.

The rotating ring 7 (not shown in FIG. 2) is coupled to a magnetic ring 13, which is freely rotatable on the outer shaft tube 10. A magnetic ring 14 is attached to the inner shaft tube 11. The magnets of the magnetic rings 13,14 are aligned so that the inner magnetic ring 14 follows a rotation of the magnetic ring 13, so that the magnetic rings 13,14 form a rotary magnetic coupling acting through the outer shaft tube 10.

The rotation of the magnetic ring 14 is transmitted through the inner shaft tube 11 to an image sensor not shown. Thus, by rotating the rotating ring 7, the orientation of the image sensor and thus the horizontal position of the image of the video endoscope 1 can be controlled.

In an alternative embodiment, the rotating ring 7 may be fixed to the outer shaft tube while the handle 5 is coupled to the magnetic ring 13. In this case, the viewing direction of the video endoscope 1 is controlled by rotating the rotating ring 7, while the horizontal position of the image is controlled with the handle 5.

The magnetic ring 13 is axially fixed on the outer shaft tube 10 between a proximal stop shoulder 20 and a distal retaining body 21.

The retaining body 21 is fixed on the outer shaft tube by means of a fastening element (i.e., fastener) 22. The retaining body 21 engages through an opening 23 of the retaining body 21 in a groove 24 of the outer shaft tube 10.

FIG. 3 shows a section along the plane A-A of FIG. 2. The outer shaft tube 10 in the area of the groove 24 and the inner shaft tube 11 can be seen.

The retaining body 21 is traversed by the opening 23 in the plane A-A except for material webs 30,31,32,33.

The fastening element 22 is a C-shaped clip and includes two arm-like end sections 34,35 and a connecting section 36. The fastening element 21 is inserted into the opening 23 in a linear motion (from above in the example shown) to fix the retaining body 21 to the outer shaft tube 10.

The distance between the end sections 34,35 at their free ends is slightly smaller than the diameter of the outer shaft tube 10 in the area of the groove 24. Therefore, during the insertion of the fastening element 22 into the opening 23, the end sections 34,35 are slightly elastically deformed outwards and spring back towards their initial shape in the final position. In this way, the fastening element is positively attached to the outer shaft tube.

The fastening element 22 may be dimensioned such that the end sections 34,35 are still somewhat under tension in the final position. In this way, the form fit is complemented by a friction fit.

In the region of the connecting section 36, a recess 40 is provided in the fastening element 22. A tool can be inserted into this recess to remove the fastening element 22 from the opening 23. The retaining body 21 can have a slight chamfer to facilitate access of a tool to the recess 40.

FIG. 4 shows a sectional view along plane B-B, which is offset in the distal direction from plane A-A. In this region, the outer shaft tube 10 has a large wall thickness and is flattened in the lower region. The retaining body 21 has a shape-complementary flattening at its inner circumference, so that the two flattenings prevent the retaining body 21 from rotating on the outer shaft tube 10.

FIG. 5 shows the section A-A already shown in FIG. 3, whereby a fastening element 122 of a different configuration is used instead of the fastening element 22. The fastening element 122 also comprises arm-like end sections 134,135 and a connecting section 136, but in contrast to the fastening element 22 it is U-shaped, i.e., the distance between the end sections 135,136 does not decrease in the direction of their free ends.

The distance between the end sections 134,135 is again slightly less than the diameter of the outer shaft tube, so that they are elastically deformed when the fastening element 122 is inserted. As a result, the fastening element 122 is frictionally secured to the outer shaft tube 10.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A video endoscope comprising:
an elongated shaft, wherein the shaft comprises at least one shaft tube,
a magnetic ring surrounding the shaft tube, the magnetic ring being rotatably arranged in a region of a proximal end of the shaft tube, the magnetic ring being axially fixed between a proximal stop shoulder of the shaft tube and a distal retaining body,
wherein the retaining body having a sleeve-like configuration and is placed on the shaft tube from a distal direction of the shaft tube towards a proximal direction of the shaft tube,
the shaft tube has an indentation in a region corresponding to the retaining body, and
the retaining body is fastened on the shaft tube by a fastener which penetrates the retaining body and extends into the indentation;
wherein an inner diameter of the retaining body is larger than an outer diameter of the shaft tube at any point between the stop shoulder and the distal end of the endoscope; and
the fastener is distal to the magnetic ring.

2. The video endoscope according to claim 1, wherein the fastener is configured to be guided a substantially linearly through the retaining body into the indentation.

3. The video endoscope according to claim 1, wherein the indentation is a circumferentially extending groove which extends along a circumferential angle of at least 180° of the shaft tube.

4. The video endoscope according to claim 3, wherein the fastener comprises one of a substantially U- or C-shaped clip.

5. The video endoscope according to claim 4, wherein the fastener engages the groove over a circumferential angle of more than 180°.

6. The video endoscope according to claim 5, wherein the fastener is elastically deformed at least temporarily during insertion into the groove.

7. The video endoscope according to claim 6, wherein the fastener is, in its fully inserted position, at least partially sprung back to its initial shape to positively hold the fastener in the groove.

8. The video endoscope according to claim 6, wherein the fastener, in its fully inserted position, is at least partially elastically deformed to frictionally hold the fastener in the groove.

9. The video endoscope according to claim 1, wherein the fastener has a recess into which a tool for removing the fastener can engage.

10. The video endoscope according to claim 1, wherein the shaft tube and the retaining body comprise form-complementary guide elements which prevent the retaining body from rotating on the shaft tube.

11. The video endoscope according to claim 3, wherein the circumferentially extending groove extends along the circumferential angle of at least 270° of the shaft tube.

* * * * *